US010603045B2

(12) United States Patent
Brown

(10) Patent No.: US 10,603,045 B2
(45) Date of Patent: Mar. 31, 2020

(54) TOURNIQUET AND METHODS OF USE AND CONSTRUCTION THEREOF

(71) Applicant: Alice M. Brown, Saginaw, MI (US)

(72) Inventor: Alice M. Brown, Saginaw, MI (US)

(*) Notice: Subject to any disclaimer, the term of this patent is extended or adjusted under 35 U.S.C. 154(b) by 89 days.

(21) Appl. No.: 15/335,647

(22) Filed: Oct. 27, 2016

(65) Prior Publication Data

US 2017/0112503 A1 Apr. 27, 2017

Related U.S. Application Data

(60) Provisional application No. 62/246,865, filed on Oct. 27, 2015.

(51) Int. Cl.
*A61B 17/132* (2006.01)
*A61B 90/00* (2016.01)

(52) U.S. Cl.
CPC ...... *A61B 17/1322* (2013.01); *A61B 17/1327* (2013.01); *A61B 2090/0807* (2016.02)

(58) Field of Classification Search
CPC ............ A61B 17/1322; A61B 17/1327; A61B 17/1325; A61B 2090/0807; A41F 9/00; A41F 9/005; A41F 9/002
See application file for complete search history.

(56) References Cited

U.S. PATENT DOCUMENTS

| | | | | |
|---|---|---|---|---|
| 2,113,534 A | * | 4/1938 | Brown | A61B 17/1327 606/203 |
| 4,273,130 A | * | 6/1981 | Simpson | A61B 17/1322 128/DIG. 15 |
| 5,615,539 A | * | 4/1997 | Graham | B68B 1/02 54/13 |
| 6,276,032 B1 | * | 8/2001 | Nortman | A44B 18/0065 24/572.1 |
| 2013/0304113 A1 | * | 11/2013 | Eikman | A61B 17/1322 606/203 |

* cited by examiner

*Primary Examiner* — Jocelin C Tanner
(74) *Attorney, Agent, or Firm* — Robert L. Stearns; Dickinson Wright, PLLC

(57) ABSTRACT

A tourniquet for occluding the flow of blood in an injured limb, and methods of use and construction thereof is provided. The tourniquet includes a strap of inelastic material having an annulus at a first end and a fastener assembly a second end. The fastener assembly is extendible through the annulus, and the strap has a hook or loop fastener portion on at least one side. The fastener assembly includes first and second fastener portions. The first fastener portion is releasably fixable to the hook or loop fastener portion on the strap and is separable from the hook or loop fastener portion under a first tensile force. The second fastener portion is fixable to the hook or loop fastener portion on the strap and is separable from the hook or loop fastener portion under a second tensile force, wherein the second tensile force is greater than the first tensile force.

8 Claims, 7 Drawing Sheets

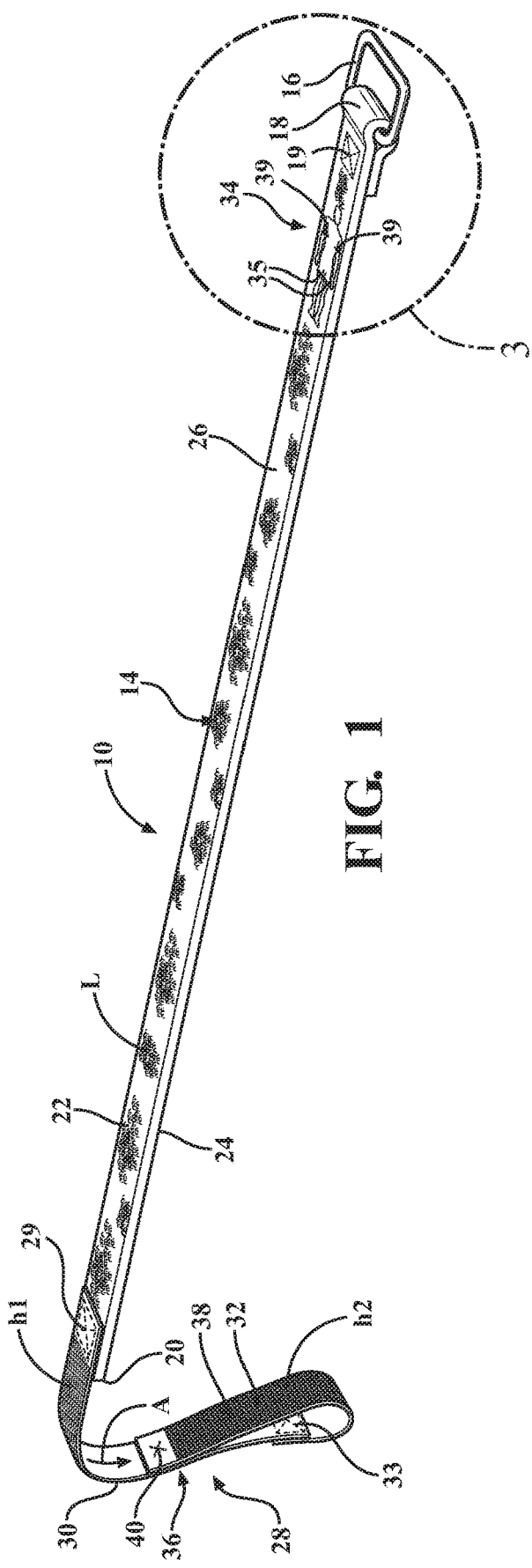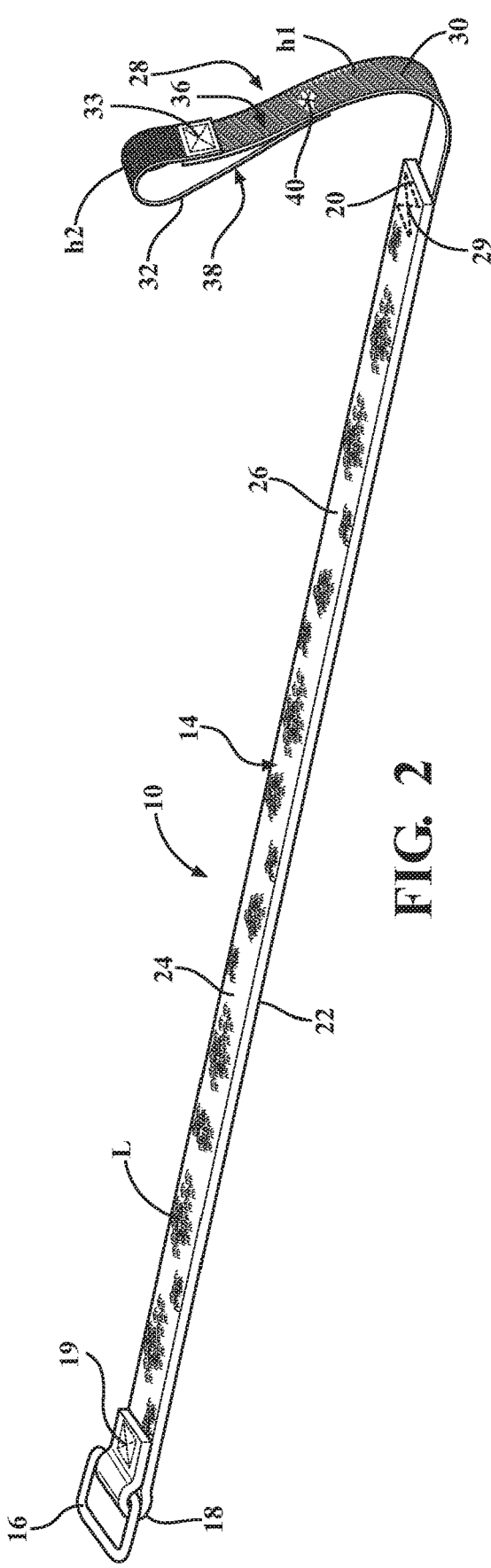

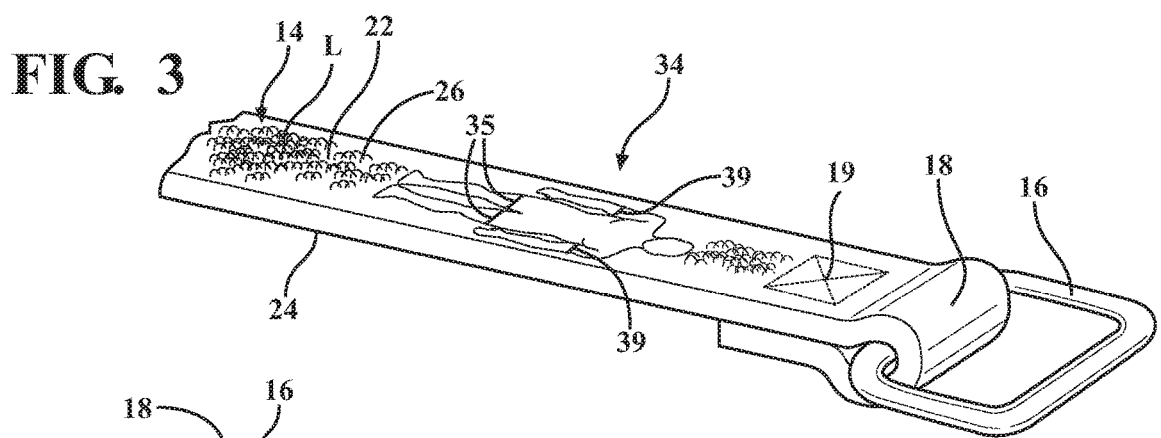
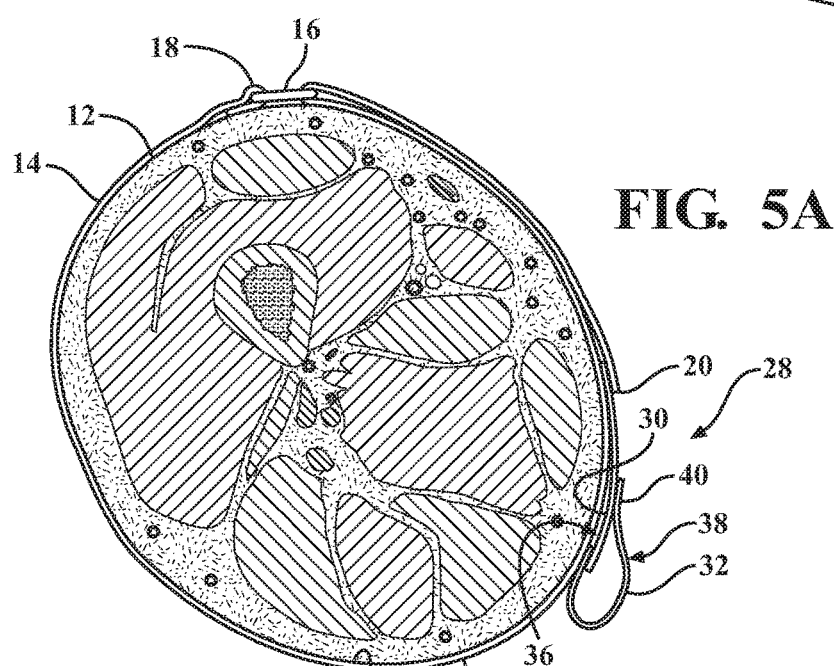
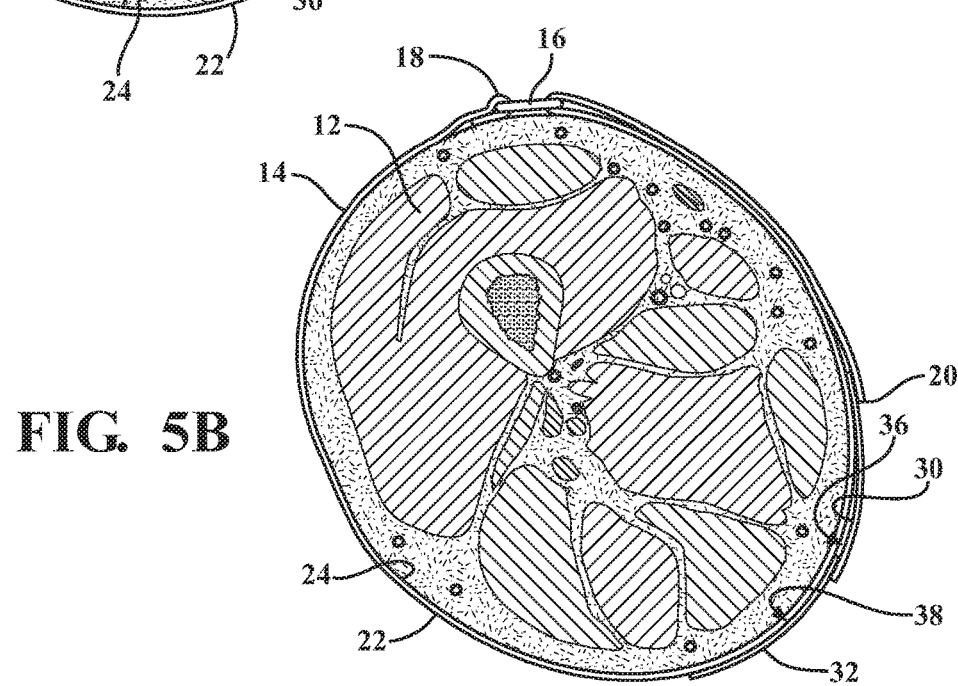

TOURNIQUET AND METHODS OF USE AND CONSTRUCTION THEREOF

CROSS-REFERENCE TO RELATED APPLICATION

This application claims the benefit of U.S. Provisional Application Ser. No. 62/246,865, filed Oct. 27, 2015, which is incorporated herein by reference in its entirety.

BACKGROUND OF THE INVENTION

1. Technical Field

This invention relates generally to devices for impeding the flow of blood in a body, and more particularly to tourniquets and to their methods of use and construction.

2. Related Art

Tourniquets are sometimes used in emergency and/or combat situations as a device to stop severe bleeding of limb of a badly injured person, such as a combat soldier or someone who has suffered a gunshot wound, a severe laceration or internal bleeding. In many cases, where a dedicated tourniquet is not readily available, a belt, shirt, shoe lace, handkerchief or similar device is often used by wrapping the item about the circumference of the injured limb at a location above the wound and is tightened, often with the aid of a stick, pipe or other rigid windlass device, to exert sufficient, uniform cuff pressure on the limb to stop the severe bleeding, including arterial bleed. Although these types of items can prove useful, they can be unreliable if not applied in just the right manner, and further, can become inadvertently loosened or in some cases removed, such as by the injured person when experiencing pain, sometimes as a result of the tourniquet itself cutting off blood flow, thereby allowing the bleeding to continue. Other known tourniquets include those that are constructed as high tech tourniquets that require in depth training, and ultimately, certification to use. Although useful, they can prove difficult to apply properly, and thus, can lead to improper use, particularly by those that lack the proper training and certification. In addition, many known tourniquets are relatively expensive as a result of mechanisms required for their construction, and further, can include rigid, relatively heavy, bulky member(s) to facilitate stoppage of blood flow, thereby occupying as much space needed to house the rigid member(s).

Accordingly, while such devices, when properly applied, can be effective in stopping blood flow of an injured extremity and keeping a severely wounded person from bleeding to death, the proper use of such tourniquets can prove challenging, while the also being relatively heavy and occupying valuable space, such as within backpacks and the like.

SUMMARY OF THE INVENTION

In accordance with one aspect of the invention, a tourniquet for occluding the flow of blood in an injured limb is provided. The tourniquet includes a strap of inelastic material having an annulus at a first end and having an opposite second end extendible through the annulus to enable the strap to be wrapped about an injured limb in need of a tourniquet. The strap has opposite sides with at least one of the sides having a hook or loop fastener portion. Further, a fastener assembly is fixed to the second end of the strap. The fastener assembly includes first and second fastener portions. The first fastener portion is releasably fixable to the hook or loop fastener portion on the strap, wherein the first fastener portion is separable from the hook or loop fastener portion under a first tensile force. The second fastener portion is fixable to the hook or loop fastener portion on the strap, wherein the second fastener portion is separable from the hook or loop fastener portion under a second tensile force, wherein the second tensile force is greater than the first tensile force.

In accordance with another aspect of the invention, the second fastener portion can be located between the first fastener portion and the strap, with the first fastener portion extending to a free end.

In accordance with another aspect of the invention, the first fastener portion can be operably attached to the strap solely via the second fastener portion, without need for additional fixing mechanisms.

In accordance with another aspect of the invention, the first fastener portion can be located between the second fastener portion and the strap, with the second fastener portion extending to a free end.

In accordance with another aspect of the invention, the second fastener portion can be initially concealed from being inadvertently attached to the strap.

In accordance with another aspect of the invention, a tourniquet for occluding the flow of blood in an injured limb is provided. The tourniquet includes a flexible strap of inelastic material having an annulus at a first end and having an opposite second end extendible through the annulus to enable the strap to be wrapped about an injured limb in need of a tourniquet. The strap has opposite sides with at least one of the sides having a hook or loop fastener portion. A fastener assembly is fixed to the second end of the strap. The fastener assembly includes first and second fastener portions. The first fastener portion is releasably fixable to the hook or loop fastener portion on the strap, wherein the first fastener portion is readily separable from the hook or loop fastener portion under a first tensile force, thereby allowing for adjustment of the constriction applied by the strap about the injured limb. The second fastener portion is fixable to the hook or loop fastener portion on the strap, wherein the second fastener portion is separable from the hook or loop fastener under a second tensile force. The second tensile force is greater than the first tensile force to the extent that removal of the strap from the injured limb is substantially prevented.

In accordance with another aspect of the invention, at least one of the sides of the strap has a loop fastener portion; the first fastener portion has a first hook fastener portion, and the second fastener portion has a second hook fastener portion, wherein the first hook fastener portion and the second hook fastener portion are different from one another.

In accordance with another aspect of the invention, at least one of the opposite sides of the strap can be provided with indicia showing the proper location on an injured limb about which to apply the strap, thereby assuring the tourniquet is applied in an optimal location to prevent the injured limb from losing blood.

In accordance with another aspect of the invention, the fastener assembly can have a preliminary application state and a finished application state, with the second fastener portion being reverse folded over or under, and/or concealed with an easily removable guard, such as a self-adhesive strip or release paper, by way of example and without limitation, when the first fastener portion is in the preliminary application state, thereby assuring the strap can remain adjustable when in the preliminary application state. The second fastener portion can be unfoldable and extendable away from the first fastener portion, or otherwise exposable for attachment to the strap in the finished application state, whereupon attachment of the second fastener portion to the strap assures the tourniquet remains fixed in its intended constricting state.

In accordance with another aspect of the invention, the second fastener portion can be releasably fixed in reverse folded relation over the first fastener portion in the preliminary application state, thereby assuring inadvertent fixing of the second fastener portion to the strap is prevented.

In accordance with another aspect of the invention, a method of occluding the flow of blood in an injured limb is provided. The method includes wrapping a strap of inelastic material about an injured limb suffering blood loss from a serious wound and reverse folding a portion of the strap through an annulus. Further, extending a fastener assembly including first and second fastener portions from an end of the strap. The first fastener portion being releasably fixable to a hook or loop fastener portion on the strap, wherein the first fastener portion is separable from the hook or loop fastener portion under a first tensile force, and with the second fastener portion being fixable to the hook or loop fastener portion on the strap, wherein the second fastener portion is separable from the hook or loop fastener portion under a second tensile force, wherein the second tensile force is greater than the first tensile force. Further yet, fixing the first fastener portion of the fastener assembly to an outwardly facing side of the strap.

In accordance with another aspect of the invention, a method of occluding the flow of blood in an injured limb is provided. The method includes wrapping a strap of inelastic material about an injured limb suffering blood loss from a serious wound and reverse folding a portion of the strap through an annulus. Then, extending a fastener assembly from the strap and fixing a first fastener portion of the fastener assembly to an outwardly facing side of the strap, wherein the first fastener portion is readily releasable from the side of the strap to allow adjustment of the constriction force applied by the strap about the injured limb. Then, ensuring the flow of the blood from the injured limb is stopped or substantially stopped. Further, fixing a second fastener portion of the fastener assembly to the outwardly facing side of the strap, wherein the second fastener portion prevents removal of the strap from the injured limb until removal under the care of medical personal.

In accordance with another aspect of the invention, the method can further include detaching the second fastener portion from being in reverse folded relation with the first fastener portion prior to fixing the second fastener portion to the outwardly facing side of the strap. While in the reverse folded relation, the second fastener portion is prevented from becoming inadvertently fixed to the outwardly facing side of the strap, thereby assuring the strap remains adjustable until the time it is desired to fixedly lock the strap about the injured limb via the second fastener portion.

In accordance with another aspect of the invention, the method can further include referencing indicia on the strap showing the proper location on an injured limb about which to apply the strap prior to wrapping the strap about the injured limb.

In accordance with another aspect of the invention, a method of constructing a tourniquet is provided. The method includes providing a strap of inelastic material with opposite sides extending lengthwise between opposite ends; operably attaching an annulus to one of the opposite ends of the strap; providing a hook or loop fastener portion extending along at least one of the opposite sides of the strap; and attaching a fastener assembly including first and second fastener portions to one of the opposite ends of the strap opposite the annulus. Further, providing the first fastener portion as being fixable to the hook or loop fastener portion on the strap and separable from the hook or loop fastener portion on the strap under a first tensile force, and providing the second fastener portion as being fixable to the hook or loop fastener portion on the strap and separable from the hook or loop fastener portion on the strap under a second tensile force, wherein the second tensile force is significantly greater than the first tensile force.

In accordance with another aspect of the invention, the method of construction can further include fixing the second fastener portion directly to the strap with the second fastener portion extending between the strap and the first fastener portion.

In accordance with another aspect of the invention, the method of construction can further include providing the hook or loop fastener portion extending along the strap as a loop fastener portion and providing the second fastener portion as a hook fastener portion fixing the second fastener portion directly to the strap solely with the loop and hook fastener portions.

In accordance with another aspect of the invention, the method of construction can further include fixing the first fastener portion directly to the strap, while leaving a portion of the first fastener portion exposed for subsequent attachment to the strap during use, with the first fastener portion extending between the strap and the second fastener portion, with the second fastener portion extending to a free end for subsequent attachment to the strap during use.

A tourniquet constructed in accordance with the invention can be easily and properly applied without training, does not require any special certification, is lightweight, such as about 0.6 oz, can be readily folded or packed into a small space for subsequent use, and prevents unwanted removal upon being secured about an injured limb.

A tourniquet constructed in accordance with the invention can include a marking or identification on end that overwraps the main strap, with a marking, either word or symbol, to show the correct direction to pull the end for correct application and to secure the strap over the bleeding limb.

BRIEF DESCRIPTION OF THE DRAWINGS

These and other aspects, features and advantages of the present invention will become more readily appreciated when considered in connection with the following detailed description of presently preferred embodiments and best mode, appended claims and accompanying drawings, in which:

FIG. 1 is a schematic perspective top view of a tourniquet constructed in accordance with one aspect of the invention shown in an unfastened, ready for use state;

FIG. 2 is a schematic perspective bottom view of the tourniquet of FIG. 1;

FIG. 3 is an enlarged fragmentary view of the encircled area 3 of FIG. 1;

FIG. 5A is a schematic cross-sectional view of the tourniquet of FIG. 1 shown in a partially fastened state about the injured limb;

FIG. 5B is a schematic cross-sectional view of the tourniquet of FIG. 1 shown in a fully fastened state about the injured limb;

DETAILED DESCRIPTION OF PRESENTLY PREFERRED EMBODIMENTS

Figure 4:
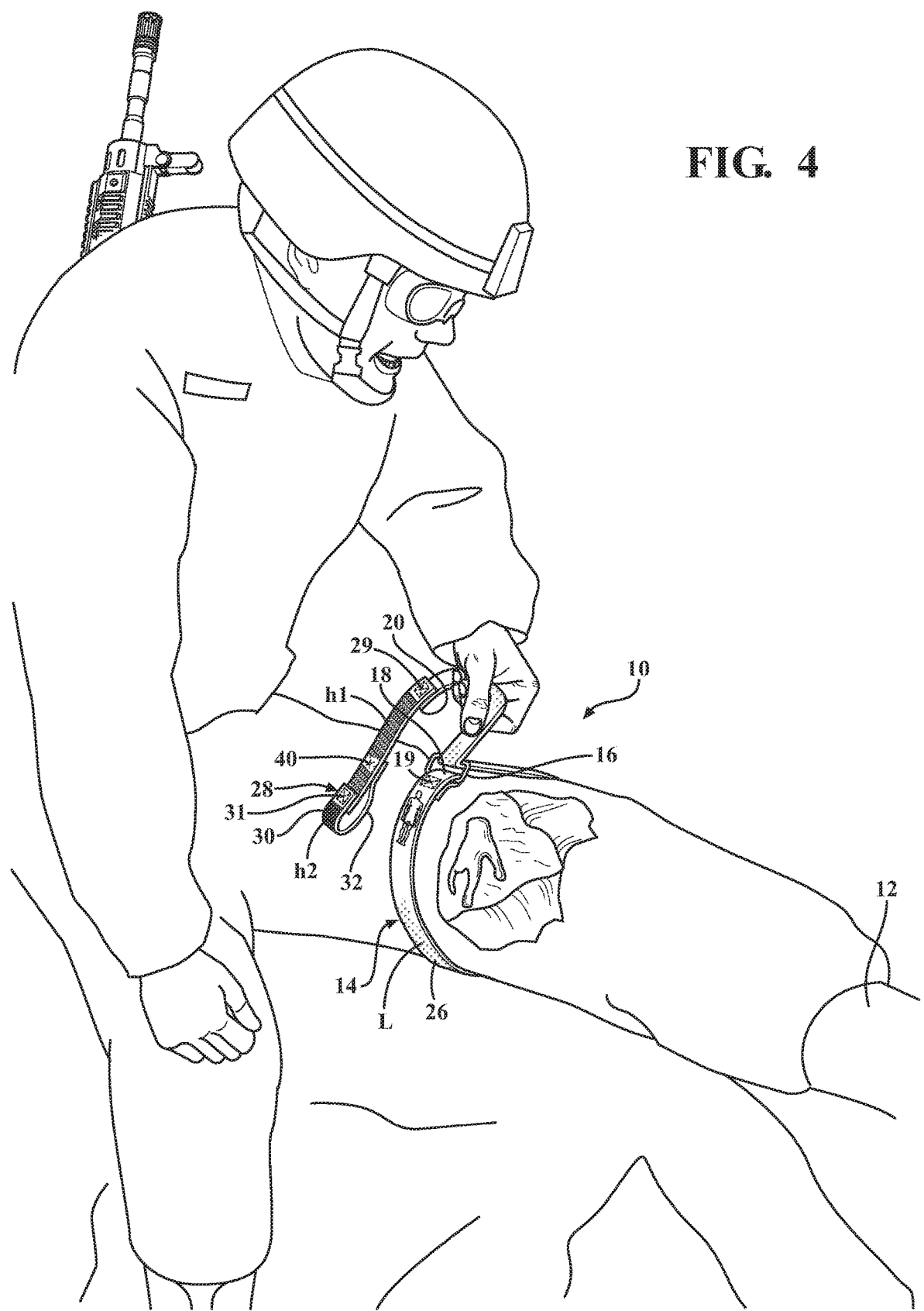
FIG. 4 is a schematic perspective view of the tourniquet of FIG. 1 shown being applied about an injured limb.
Figure 6:
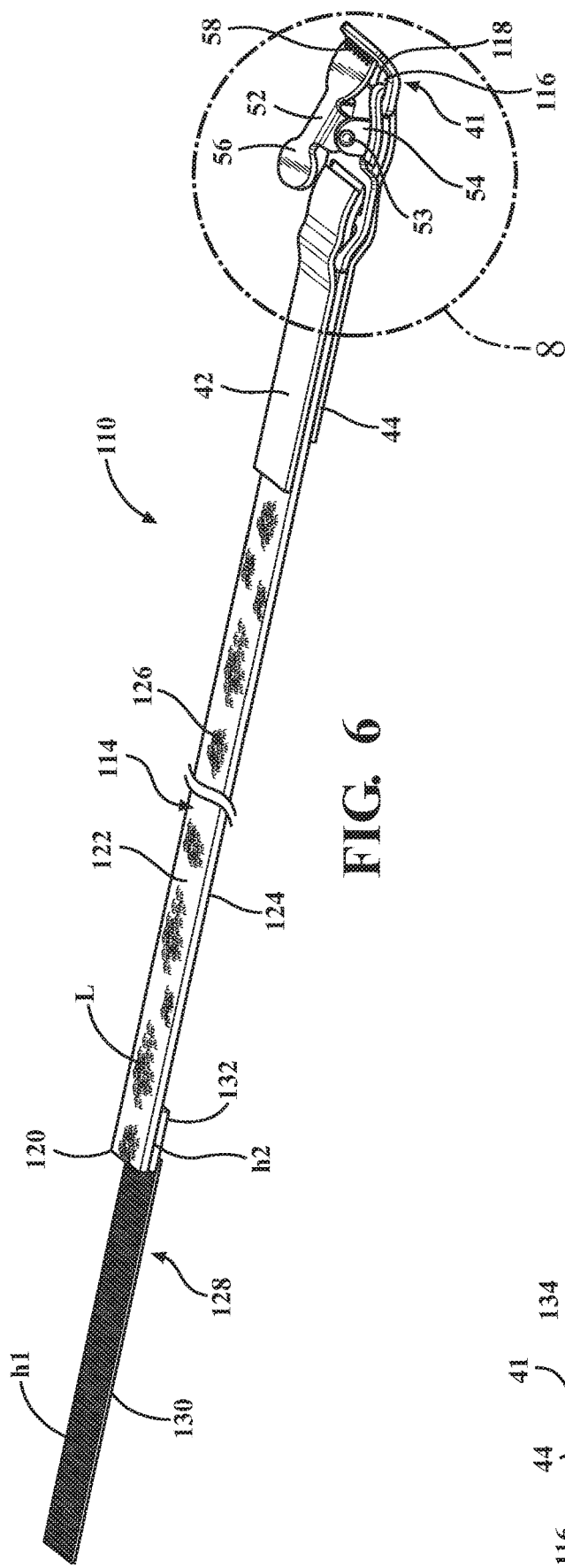
FIG. 6 is a schematic perspective top view of a tourniquet constructed in accordance with another aspect of the invention shown in an unfastened, ready for use state.
Figure 7:
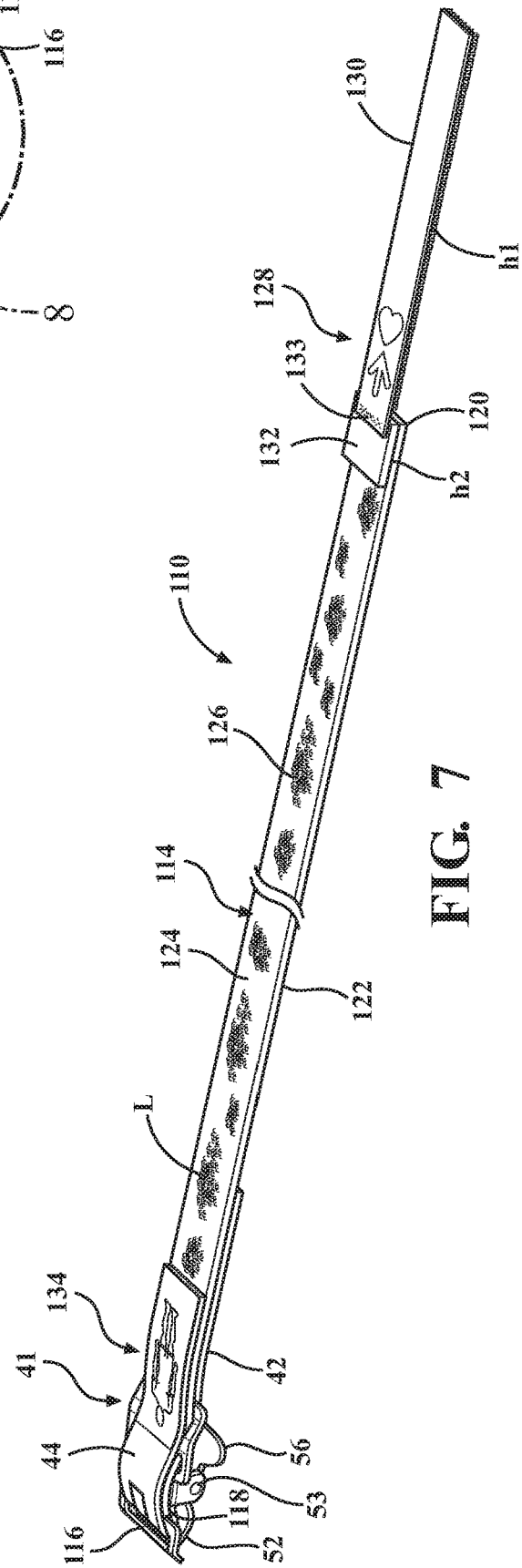
FIG. 7 is a schematic perspective bottom view of the tourniquet of FIG. 6.
Figure 8:
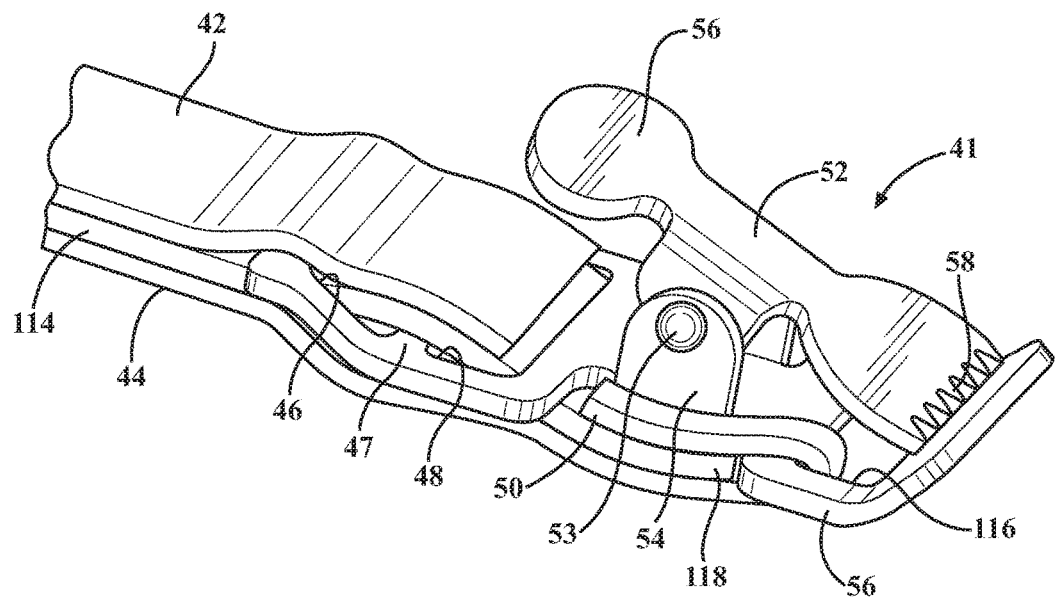
FIG. 8 is an enlarged fragmentary view of the encircled area 3 of FIG. 1.

Referring in more detail to the drawings, FIGS. 1, 2 and 4 illustrate a tourniquet 10, constructed in accordance with one aspect of the invention, for occluding the flow of blood in an injured limb 12. The tourniquet 10 includes a strap 14 of flexible, highly inelastic material having an annulus 16, such as a closed or substantially closed loop of metal or polymeric material fixed at a first end 18, such as via a stitching 19 or otherwise, as desired, and having an opposite second end 20 extendible through the annulus 16 to enable the strap 14 to be wrapped about the injured limb 12 in need of a tourniquet. The strap 14 has opposite sides 22, 24 with at least one side, and preferably both sides 22, 24 having a hook or loop fastener portion, constructed as a loop fastener portion 26, having a plurality of loops (L), in a preferred embodiment. A fastener assembly 28 is fixed to the second end 20 of the strap 14, such as via a stitching 29 or otherwise, as desired. The fastener assembly 28 includes a first fastener portion 30 and a second fastener portion 32 fixed to one another, such as via a stitching 33 or otherwise, as desired. The first fastener portion 30 is fixable to the hook or loop fastener portion 26 with a marking A, either word or symbol, to show direction to pull, shown as a loop fastener portion 26 on the strap 14, wherein the first fastener portion 30, including a plurality of hooks (h1), is readily separable from the loop fastener portion 26 under a first peel force F1, thereby allowing for quick and easy adjustment of the constriction force applied by the strap 14 about the injured limb 12. The second fastener portion 32, having a plurality of hooks (h2), is fixable to the loops L of the loop fastener portion 26 on the strap 14, wherein the second fastener portion 32 is separable from the loop fastener portion 26 under a second peel force F2. The second peel force F2 is significantly greater than the first peel force F1, due to the hooks h1, h2 being different from one another, to the extent that removal of the strap 14 from the injured limb 12, upon being fully secured thereabout, is substantially prevented, and is preferably only permitted via cutting or otherwise severing the strap 14 along its length, such as desired when in the presence of medical personnel.

The strap 14 is of sufficient length to enable the strap 14 to be wrapped about the circumference of the injured limb 12, such as a person's limb. The strap 14 may have a length of from 8 inches to 36 inches, by way of example and without limitation. The exact length of the strap 14 is not critical so long as it fits in a reverse wrapped configuration about the user's injured limb, and it will be appreciated by those of ordinary skill in the art that the desired length can be chosen to fit a particular person or general size of person (e.g., small, medium, large and/or extra-large) so as to have a selection of such devices with straps of differing length, or the length can be chosen to fit limbs of a variety of sizes (e.g., adult biceps in the case where the limb is an arm to adult thighs in the case where the limb is a leg, and of various sizes thereof). The high inelasticity of the strap 14 provides the strap 14 with a low extensibility, also referred to as elongation, defined as the percent (%) increase in length from the original length at which the material breaks, and can be provided between about 2-10%, and preferably between about 2-5%, by way of example and without limitation. Further, the strap 14 has a high tensile strength and high Young's Modulus of Elasticity, which is derived via Hook's Law (stress being directly proportional to strain), with Young's Modulus of Elasticity being represented by the formula: $E=\sigma/\varepsilon$, $\sigma$=stress (force/area) and $\varepsilon$=strain (change in length/original length). Accordingly, having a high Young's Modulus of Elasticity (E) means the strap 14 is able to withstand a high amount of stress while at the same time exhibit a low amount of strain. The materials used to construct the strap 14 can be natural (organic), such as carbon fibers, and/or synthetic (inorganic), such as polymeric fibers, e.g. polyethylene terephthalate (PET), by way of example and without limitation. If formed of fibers, also referred to as yarns, including monofilament and/or multifilaments, the strap 14 can be woven to provide the aforementioned high Young's Modulus of Elasticity (E). Otherwise, it is contemplated herein that the strap 14 could be made as a solid sheet of extruded material, or otherwise. Accordingly, the strap 14 is ensured to provide the constricting hoop force necessary to function as a tourniquet, with the constricting force being maintained, without strain or relaxation, until it is desired to remove the tourniquet 10.

In application, the fastener assembly 28 and second end 20 of the strap 14 may be readily extended through the annulus 16, as indicated via arrow A (FIG. 1), so as to form a closed loop or circle with the strap 14, and then further drawn through the annulus 16 and back on itself in reverse fashion to tighten or cinch the strap 14 to reduce its effective diameter of the loop (FIG. 4). In order to ensure the tourniquet 10 is fixed about the proper location of the person's limb, whether an arm or leg, indicia 34 is provided on the strap 14, shown as being adjacent the first end 18, by way of example and without limitation. The indicia 34 shows the proper location 35 as being high up on the thigh for a leg injury, and the proper location 37 as being above the bicep for an arm injury. These locations 35, 37 provide the optimal locations for stopping the flow of blood through the respective limbs, regardless of the location of the injury on the limb. The strap 14 can be tightly cinched by drawing the second end 20 of the strap 14 back on itself in reverse fold or drawing fashion through the annulus 16. The strap 14 can be initially secured in a preliminary position estimated to be a fully tightened position by means of the first fastener portion 32, including a first hook fastener portion 36, wherein the hooks h1 of the first hook fastener portion 36 are releasably fixed to the loops L of the loop fastener portion 26 on an outwardly facing side 22 of the strap 14 (FIG. 5A), such as from a standard Velcro® hook and loop fastener, e.g. hook 65, 88, and loop 1000, 2000, having a peel strength ranging between about 0.35-1.2 psi; a shear strength ranging between about 7.5-14 psi; and a tension strength ranging between about 6.5-8.5 psi. It should be recognized that the loop fastener portion 26 on the strap 14 may extend along the full length, or substantially full length of the strap 14, thereby providing the strap 14 with a great range of adjustability to fit limbs of various diameters (arms to legs, small to large in diameter). If it is determined that the preliminary position is not tight enough to stop or substantially stop the flow of blood from the limb 12, the hooks h1 of the first hook fastener portion 36 may be ready detached from the loops L of the loop fastener portion 26 on the strap 14 under an easily applied removal peel force F1, whereupon the strap 14 may be further tightened and refastened via the first hook fastener portion 36. This process is continued until it is determined that the strap 14 is constricted enough in diameter to stop the flow of blood from the limb.

Upon being fixed in a proper position to stop the flow of blood from the limb 12 (FIG. 5A), then and only then, the hooks h2 of the second fastener portion 32 can be fixed to the loops L of the loop fastener portion 26 on the strap 14, wherein the hooks h2 are on a second hook fastener portion 38 of the second fastener portion 32 (FIG. 5B), such as sold under the tradename Vel-Lock® P87 or Velcro® P87S, having a peel strength of about 3 psi; a shear strength of about 80 psi; and a tension strength of about 18 psi, by way of example and without limitation, to bring the tourniquet 10 to a finished and fixed application state. Accordingly, once the second hook fastener portion 38 is fixed to the loop fastener portion 26, as discussed above, the second fastener portion 32 can only be removed from the strap 14 under a second peel strength F2 which is generally more than a person can apply, particularly when injured, and thus, in order to remove the tourniquet 10, it is preferably cut via medical staff personnel, such as via scissors or some other cutting instrument. Accordingly, the finished state of attachment of the tourniquet 10 about the limb 12 prevents the injured person from intentionally or unintentionally dislodging or removing the tourniquet 10, which is known to be done as a result of pain. Of course, even though painful, the tourniquet 10 must remain in place to prevent further bleeding from the limb 12.

To prevent the hooks h2 of the permanent second fastener portion 32 from becoming inadvertently attached to the loops L of the loop fastener portion 26 on the strap, the second fastener portion 32 is preferably releasably fixed in a position to prevent such an occurrence, such as by being reverse folded over the first fastener portion 30. As shown in FIGS. 1, 2 and 5A, the second fastener portion 32 is releasably fixed in a reverse folded position, such a via a tack stitch 40 or other temporary, frangible fixation mechanism. Otherwise, it is contemplated herein that the hooks h2 of the second fastener portion 32 could be covered with a guard for subsequent removal, when desired to fix the hooks h2 of the second fastener portion 32 in position, such as via a self-adhesive strip, cover, sheath, or release paper, by way of example and without limitation. Upon being determined that the tourniquet 10 is in a properly constricted position about the limb 12, the frangible fixation mechanism 40 can be easily broken, or the hooks h2 of the second fastener portion 32 can be otherwise exposed, whereupon the second fastener portion 32 can be unfolded away from the first fastener portion 30, or unshielded/uncovered, for permanent fixation to the loop fastener portion 26 on the strap 14.

In accordance with another aspect of the invention, the tourniquet 10 can include a marking indicating "long transport time" or the like, if it is determined by the medical staff or field personnel that the limb is not able to be saved or repaired, or indicating "short transport time" or the like, if it believed that the limb can be saved or repaired. The time to permanent damage of a limb having a tourniquet is universally accepted to be 78 minutes from application of the tourniquet to removal of the tourniquet. Thus, if the limb is believed to be salvageable, it is critical for the tourniquet to remain on the limb less than 78 minutes, thus providing the benefit of having the marking indicating "short" or "long" transport time.

In FIGS. 6, 7 and 10-11, a tourniquet 110, constructed in accordance with another aspect of the invention, is shown, wherein the same reference numerals as used above, offset by a factor of 100, are used to identify like features. One skilled in the art will readily appreciate the commonalities of the tourniquets 10, 110, and thus, the discussion hereafter is largely devoted to some differences in construction between the tourniquets 10, 110, with some redundancy included for general overview.

The tourniquet 110 includes a strap 114 of flexible, highly inelastic material, as discussed above, having an annulus 116 provided in a spring clip, also referred to as spring buckle or simply buckle 41, at a first end 118 and having an opposite second end 120 extendible through the annulus 116 of the buckle 41 to enable the strap 114 to be cinched and fastened about an injured limb 112 in need of a tourniquet. The strap 114 has opposite sides 122, 124 with at least one side, and shown as both sides 122, 124 having a hook or loop fastener portion, constructed as a loop fastener portion 126 having a plurality of loops L in a preferred embodiment. A fastener assembly 128 is fixed to the second end 120 of the strap 114, wherein the fastener assembly 128 includes a first fastener portion 130 and a second fastener portion 132. The first fastener portion 130 is fixable to the hook or loop portion, shown as a loop fastener portion 126 on the strap 114, wherein hooks h1 of the first fastener portion 130 are separable from the loops L of the loop fastener portion 126 under a first peel force F1, thereby allowing for adjustment and selective removal of the constriction force applied by the strap 114 about the injured limb 112, as desired. The second fastener portion 132 is fixable to the loop fastener portion 126 on the strap 114 to fix and maintain the first fastener portion 130 and second fastener portion 132 in permanently fixed relation to the strap 114, wherein hooks h2 of the second fastener portion 132 are only separable from the loops L of the loop fastener portion 126 under a second peel force F2 that is significantly greater than the first peel force F1, to the extent that removal of the second fastener portion 132 from the strap 114 is substantially prevented. The second fastener portion 132 is fixed directly to the strap 114 via the respective hooks h2 on the second fastener portion 132 and the loops L on the strap 114, and the first fastener portion 130 is fixed directly to the second fastener portion 132, such as via stitching 133, by way of example and without limitation. Accordingly, the second fastener portion 132 extends between the first fastener portion 130 and the strap 114 to operably connect the first fastener portion 130 to the strap 114. As such, the first fastener portion 130 can be fixed to the strap 114 without need for further fasteners other than the second fastener portion 132, though it is contemplated that a supplemental, redundant fastener could be employed to fix the second fastener portion 132 to the strap 114, such as a stitching or adhesive, by way of example and without limitation.

Figure 9:
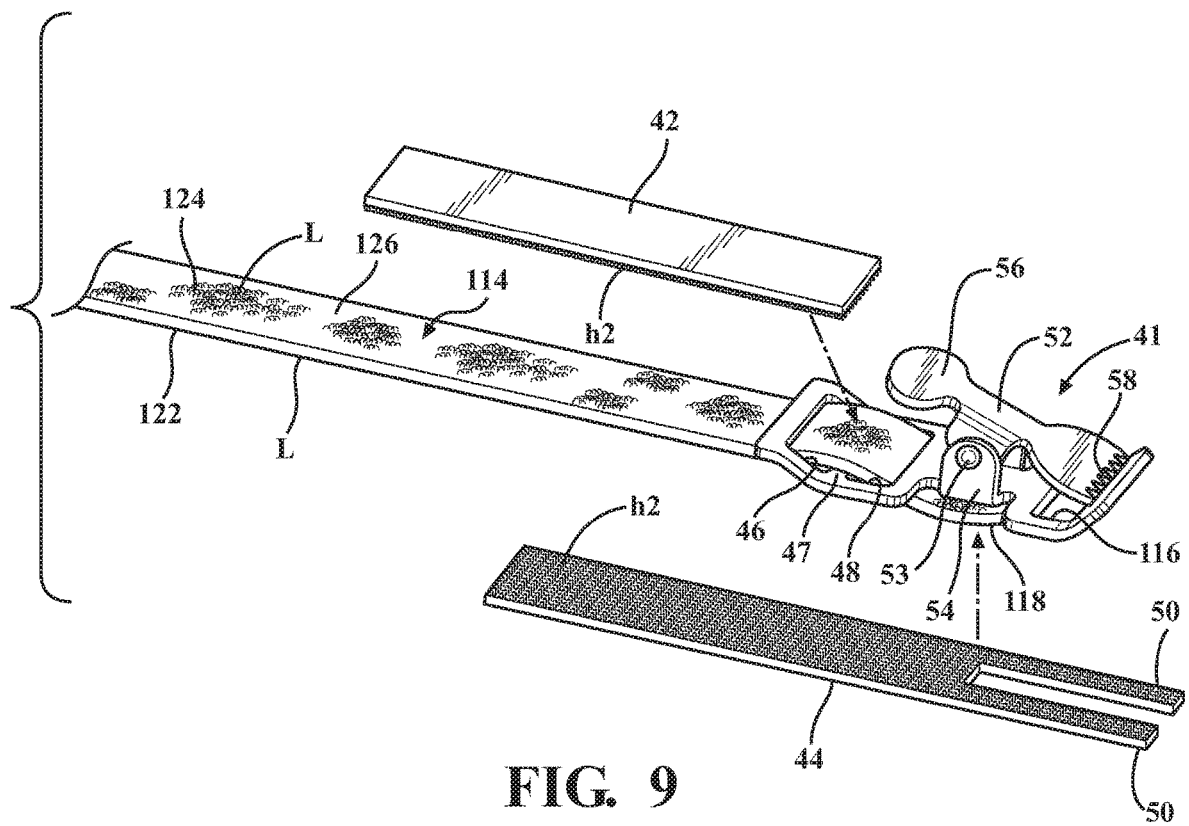
FIG. 9 is a partially exploded view of FIG. 8.

The spring buckle 41 can be fixed to the first end 118 via at least one, and shown as a plurality of pieces of hook material fasteners, identified hereafter as an upper fastener 42 and a lower fastener 44. The upper and lower fasteners 42, 44 are provided as separate pieces or strips of the same inelastic hook material as used for the inelastic second fastener portion 132, thereby including hooks h2. As best shown in FIG. 9, the first end 118 of the strap 114 is disposed upwardly through a first opening 46, over a laterally extending bar or band 47, and then downwardly through a second opening 48. Then, with the first end 118 fed through the openings 46, 48, the hooks h2 of the upper hook material 42 are pressed into fixed attachment with the loops L on the side 124 of the strap 114 to cover the openings 46, 48 and the band 47 and the hooks h2 of the lower hook material 44 are pressed into fixed attachment with the loops L on the opposite side 122 of the strap 114 to cover the openings 46, 48 and the band 47. In addition to pressing the lower hook material 44 into fixed attachment with the strap 114, a pair of forked or bifurcated end strips 50 of the lower hook material 44 is fed upwardly through the annulus 116 and reverse wrapped into fixed attachment with the loops L on the side 126 of the strap 114. As a result, the bifurcated end strips 50 prevent the first end 118 of the strap 114 from being pulled outwardly from the openings 46, 48 of the spring clip 41, and thus, act to retain the spring clip 41 in permanently attached relation to the strap 114. It is contemplated herein that the bifurcated end strips 50 could be provided as separate pieces of material from the lower hook material 44, if desired.

Figure 10:
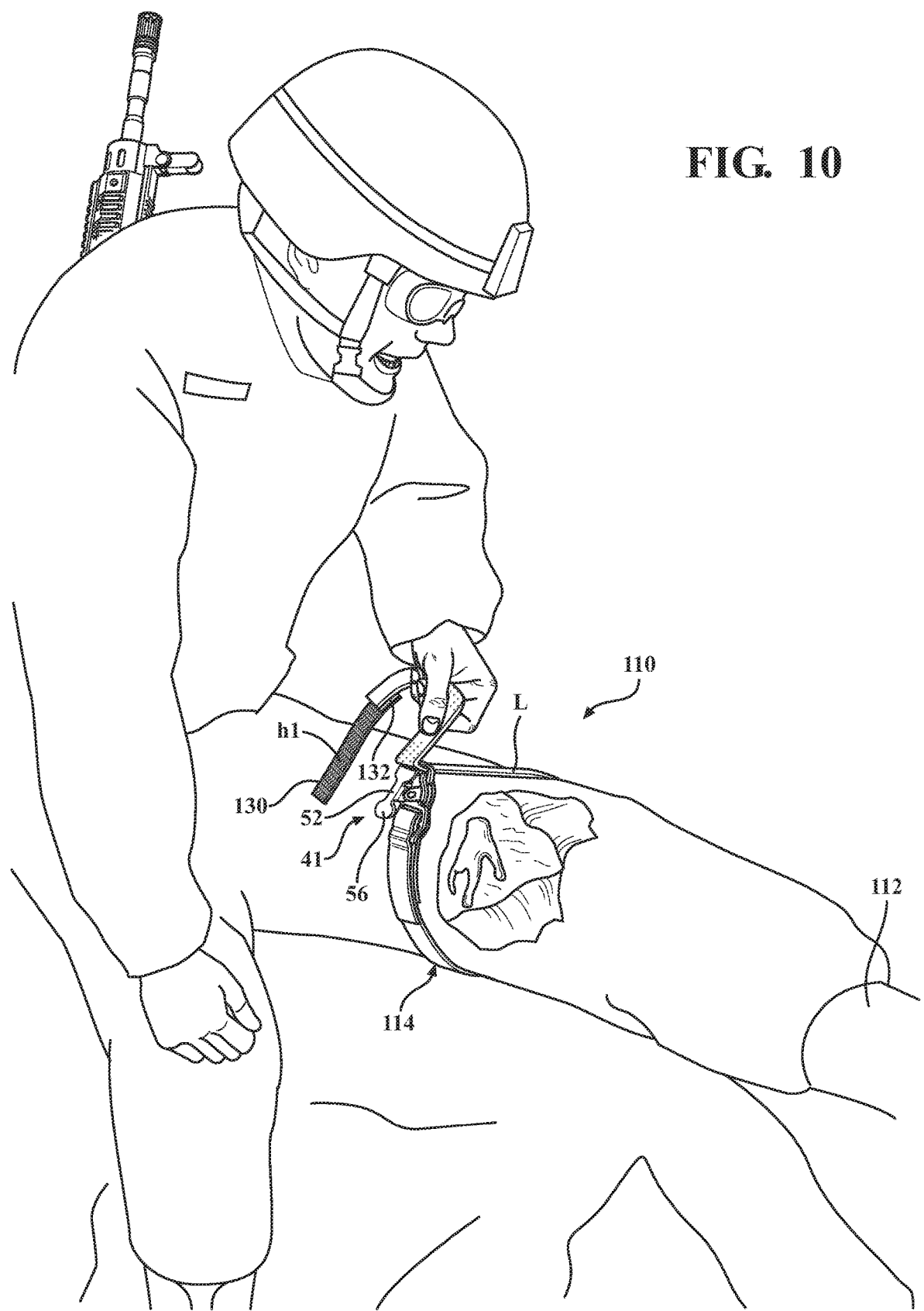
FIG. 10 is a schematic perspective view of the tourniquet of FIG. 6 shown being applied about an injured limb.
Figure 11:
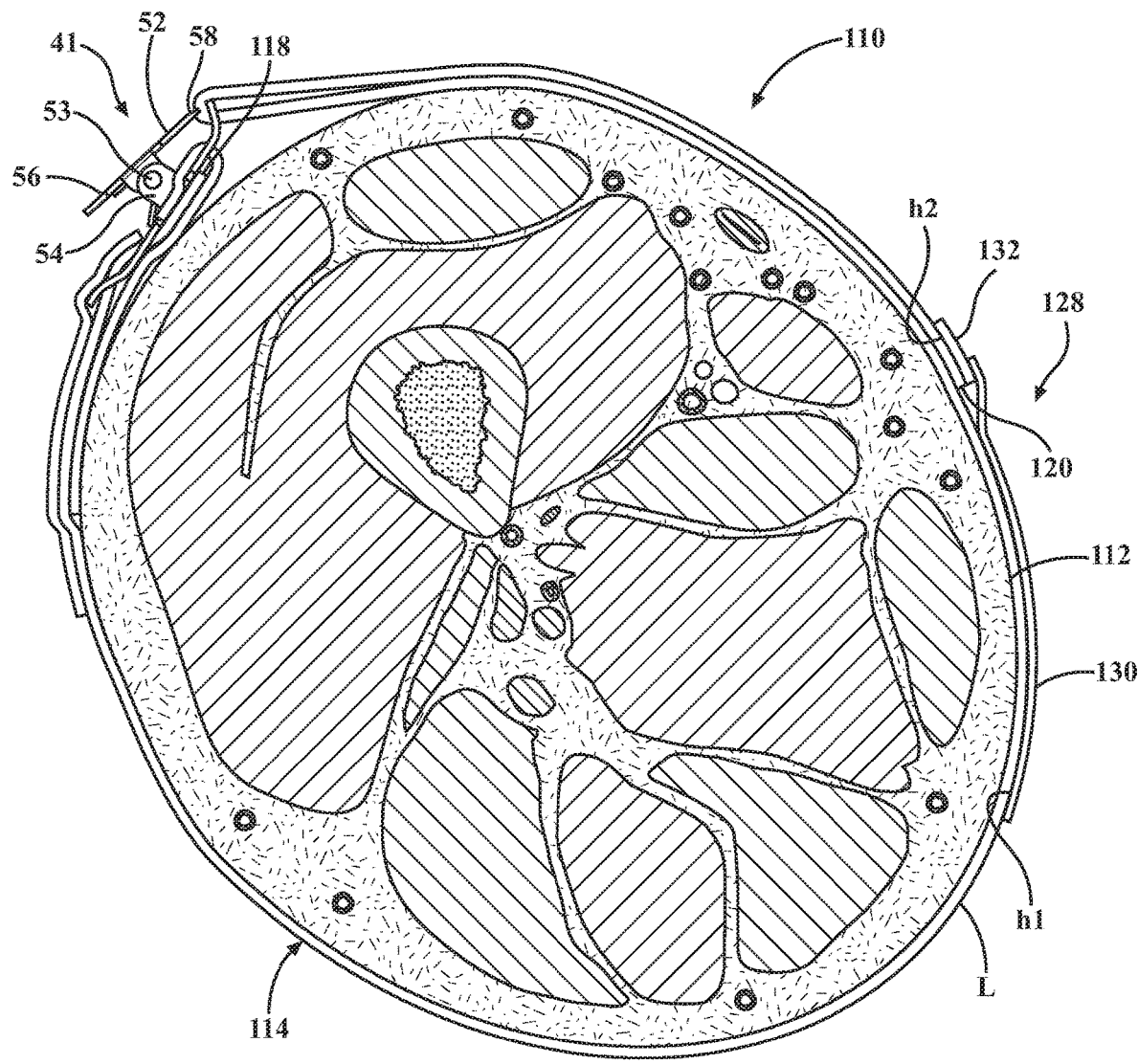
FIG. 11 is a schematic cross-sectional view of the tourniquet of FIG. 6 shown in a fully fastened state about the injured limb.

The spring buckle 41 includes a spring biased clip 52 pivotally supported via pins or rivets 53 on flange members 54 of the buckle 41. The clip 52 is biased into a closed, locked position, thereby bringing the clip 52 into a tightly clamped relation with a main body of the buckle 41, and can be readily depressed via pressing on a depress tab 56 to move against the bias of a spring member (not shown) to an open, unlocked position. While inserting the first end 118 of the strap 114 through the annulus 116, the depress tab 56 is depressed to move the clip 52 to its open, unlocked position, whereupon the strap 114 can be readily fed and pulled through the annulus 116 to reduce the effective diameter of a closed loop portion the strap 114. Even while the clip 52 is in the closed, locked position, after the first end 118 of the strap 114 has been fed through the annulus 116, the strap 114 can be pulled and cinched to a tighter, reduced effective diameter, as shown in FIG. 10, as pulling the strap 114 to reduce the effective diameter tends to freely move the clip 52 against the bias of the spring toward the open, unlocked position. However, it is to be recognized that the strap 114 is substantially prevented from being pulled in an opposite direction tending to increase the effective diameter of the strap 114 when the clip 52 is in its closed, locked position. This results due to teeth 58 of the clip 52 being driven into the material of the strap 114 as the clip 52 is being pulled increasingly toward a tighter, closed, locked position. Accordingly, to pull the strap 114 outwardly from the annulus 116, the clip 52 must be depressed to its open, unlocked position.

In application, the fastener assembly 128 and second end 120 of the strap 114 may be readily extended through the annulus 116, with the clip 52 initially being depressed to the open, unlocked state, so as to form a closed loop with the strap 114, and then further drawn through the annulus 116, with the clip 52 being in either the open or closed states, and back on itself in reverse fashion to tighten or cinch the strap 114 to reduce its effective diameter (FIG. 10). In order to ensure the tourniquet 110 is fixed about the proper location of the person's limb, whether an arm or leg, indicia 134 is provided on the strap 114, shown as being adjacent the first end 118, as discussed above. The strap 114 can be tightly cinched by drawing the second end 120 of the strap 114 back on itself in reverse fashion through the annulus 116 while the clip 52 remains in its closed, locked state, thereby preventing the strap 114 from inadvertently loosening as it is being tightened and upon being fully tightened. Upon the strap 114 being tightened to the desired tightness about the limb 12 to stop or substantially stop the flow of blood from the limb 12, the first hook fastener portion 136 may be ready fastened via the first hook fastener portion 136 to the loops on the strap 114. This process can be repeated as necessary until it is determined that the strap 114 is constricted enough in diameter to stop the flow of blood from the limb.

Many modifications and variations of the present invention are possible in light of the above teachings. It is, therefore, to be understood that the invention may be practiced otherwise than as specifically described, and that the scope of the invention is defined by any ultimately allowed claims.

What is claimed is:

1. A tourniquet for occluding blood flow in an injured limb, comprising:
   a strap wrappable about the injured limb;
   said strap having a loop pile fastener portion;
   said strap having a first hook fastener portion that is engageable with said loop pile fastener portion;
   said strap having a second hook fastener portion of a that is engageable with said loop pile fastener portion;
   said first and second hook fastener portions being of different construction;
   said first hook fastener portion having an associated first peel strength value measured in pounds per square inch;
   said second hook fastener portion having an associated second peel strength value measured in pounds per square inch;
   said second peel strength value being greater than that of said first peel strength value, wherein separation by peeling of said second hook fastener portion from said loop pile portion requires application of a greater force than is required to separate by peeling said first hook fastener portion from said loop pile fastener portion and, wherein said second hook fastener portion is reverse folded over said first hook fastener portion in a preliminary application state and said second hook fastener portion is unfolded and extending away from said first hook fastener portion in a finished application state.

2. The tourniquet of claim 1 wherein said strap has indicia adjacent a first end, said indicia showing a proper location on an injured limb about which to apply said strap.

3. The tourniquet of claim 2 wherein said strap has a symbol indicating a direction in which the strap is to be pulled for correct application.

4. The tourniquet of claim 1 wherein said second hook fastener portion is releasably fixed in reverse folded relation over said first hook fastener portion in said preliminary application state.

5. The tourniquet of claim 1 wherein said second hook fastener portion is at a free end.

6. The tourniquet of claim 5 wherein said second hook fastener portion is operably fixed to said strap by said first hook fastener portion.

7. The tourniquet of claim 1 further including a spring clip fixed to a first end of said strap, said spring clip forming an annulus through which an opposite free end of said strop is extended to enable the strap to be positioned about the injured limb.

8. The tourniquet of claim 7 further including a hook material extending through said annulus and being fixed to said loop fastener portion of said strap to fix said spring clip to said strap.

\* \* \* \* \*